(12) United States Patent
Sunohara et al.

(10) Patent No.: US 7,524,417 B2
(45) Date of Patent: Apr. 28, 2009

(54) DIALYZER AND METHOD FOR MANUFACTURING THE SAME

(75) Inventors: Takashi Sunohara, Osaka (JP); Hidehiko Anbo, Osaka (JP); Toshiaki Masuda, Osaka (JP)

(73) Assignee: Nipro Corporation, Osaka (JP)

( * ) Notice: Subject to any disclaimer, the term of this patent is extended or adjusted under 35 U.S.C. 154(b) by 204 days.

(21) Appl. No.: 10/743,747

(22) Filed: Dec. 24, 2003

(65) Prior Publication Data

US 2004/0149645 A1 Aug. 5, 2004

(30) Foreign Application Priority Data

Dec. 26, 2002 (JP) ............................. 2002-378262

(51) Int. Cl.
*B01D 61/28* (2006.01)

(52) U.S. Cl. ............. 210/321.79; 210/232; 210/321.89; 210/500.23

(58) Field of Classification Search ............. 210/321.6, 210/321.72, 321.78, 321.79, 321.8, 321.81, 210/321.88, 321.89, 321.9, 232, 455, 500.23

See application file for complete search history.

(56) References Cited

U.S. PATENT DOCUMENTS

| 4,219,426 A | 8/1980 | Spekle et al. ................ 210/232 |
| 4,308,654 A * | 1/1982 | Bogart .......................... 29/451 |
| 6,251,275 B1 * | 6/2001 | Rekers ................... 210/321.78 |

FOREIGN PATENT DOCUMENTS

| EP | 0 701 826 A2 | 3/1996 |
| EP | 1 344 542 A1 | 9/2003 |
| FR | 2 267 138 | 11/1975 |
| FR | 2 542 203 | 9/1984 |
| JP | SHO-52-138071 | 11/1977 |
| JP | 7-59849 A | 3/1995 |
| JP | 8-168525 A | 7/1996 |
| JP | 8-192031 A | 7/1996 |
| JP | 11-394 A | 1/1999 |
| JP | 11-9684 A | 1/1999 |
| JP | 11-319079 A | 11/1999 |
| JP | 11-319080 A | 11/1999 |
| JP | 2000-210538 | 8/2000 |
| JP | 2003-220134 | 8/2003 |
| WO | 98/22161 A1 | 5/1998 |

OTHER PUBLICATIONS

English translated French Patent No. 2 267 138.*
English translation French Patent No. 2542203.*
Gejyo, F. et al., "New Form of Amyloid Protein Associated with Chronic Hemodialysis Was Identified as $\beta_2$-Microglobulin", *Biochemical and Biophysical Research Communications*, vol. 129, No. 3, 1985, pp. 701-706.
Baurmeister, U. et al., "High-flux Dialysis Membranes: Endotoxin Transfer by Backfiltration Can Be a Problem", *Nephrol Dial Transplant*, v. 4, Supplement, 1989, pp. 89-93.

* cited by examiner

*Primary Examiner*—John Kim
(74) *Attorney, Agent, or Firm*—Kubovcik & Kubovcik

(57) ABSTRACT

A dialyzer including a substantially cylindrical case 2, a hollow fiber bundle 3 made of a plurality of hollow fiber membranes provided in the case 2, a blood flow path formed by lumens of the hollow fiber membranes, a dialysate flow path formed by a gap between the inner wall of the case 2 and the hollow fiber membranes, and a cylindrical elastic tube 4 inserted in the gap between the inner wall of the case 2 and the hollow fiber bundle 3.

6 Claims, 7 Drawing Sheets

X-X

Y-Y

DIALYZER AND METHOD FOR MANUFACTURING THE SAME

FIELD OF THE INVENTION

The present invention relates to a dialyzer used in dialysis. More specifically, it relates to an internal filtration accelerating-type dialyzer which can increase an internal filtration rate and an internal backfiltration rate within the dialyzer.

BACKGROUND OF THE INVENTION

For therapy of patients whose renal function is impaired, for example, patients whose function of removing waste products or the like in blood is impaired because of renal insufficiency or the like, therapy by blood purification such as hemodialysis or hemodialysis filtration has so far been performed. In this blood purification therapy, urea, creatinine, uric acid, low-molecular proteins, water and the like accumulated in blood are removed by bringing the blood into contact with a dialysate through semipermeable membranes in a dialyzer.

In recent years, a substance that causes amyloidosis, which is one of the complications in dialysis, has been identified as $\beta_2$ microglobulin having a molecular weight of 11,800 (Gejyo F. et al. Biochem. Biophys. Res. Commun. 1985: 129: 701-706). Since $\beta_2$ microglobulin having a high molecular weight has a low diffusion rate, removal efficiency is higher by hemofiltration than by hemodialysis. Further, since a substance having a low molecular weight, such as urea, has a high diffusion rate, removal efficiency is higher by hemodialysis than by hemofiltration. Accordingly, a hemodialysis filtration (HDF) therapy, which is a combination of hemodialysis and hemofiltration, has been conceived. In the HDF therapy, filtration of a large amount of blood is conducted with a dialyzer and a replenisher is supplied in a blood circuit. Therefore, an exclusive device with a complicated structure is required.

Meanwhile, a dialyzer excellent in substance permeability and water permeability, which can remove $\beta_2$ microglobulin having a high molecular weight, has been developed. It has been found that such a dialyzer excellent in substance permeability and water permeability allows filtration and backfiltration between blood and a dialysate via a semipermeable membrane (hereinafter referred to as internal filtration and internal backfiltration) even when forced filtration by dewatering is not performed (U. Bauremeister et al., Nephrol Dial Transplant. Suppl., 1989). Accordingly, a hemodialysis filtration method that performs filtration and replenishment by increasing an amount of internal filtration and an amount of internal backfiltration has been proposed. Additionally, an internal filtration accelerating-type dialyzer capable of increasing dialysis efficiency, which is used in the hemodialysis filtration method, is being developed.

Usually, the internal filtration and the internal backfiltration do not occur at a same position within a dialyzer. Since blood and a dialysate are passed through a dialyzer in directions opposite to each other, a fluid having a higher pressure moves to a fluid having a lower pressure via a semipermeable membrane regarding the blood and the dialysate. That is, there is a tendency that the internal filtration occurs on a blood inflow side within a dialyzer and the internal backfiltration occurs on a blood outflow side within a dialyzer.

For increasing an internal filtration rate and an internal backfiltration rate in a dialyzer, it is necessary to increase a pressure loss along a blood flow path or a dialysate flow path. The pressure loss along the flow path is represented by the Hagen-Posuille formula which is a pressure loss inducing formula of a laminar flow in a cylindrical tube:

$$\Delta P = 8\mu L Q/\Pi R^4$$

($\Delta P$: pressure loss along a flow path, $\mu$: viscosity of a fluid, $L$: length of a flow path, $R$: radius of a flow path, $Q$: volume flow rate).

It is found that to increase the pressure loss $\Delta P$ along the flow path, the volume flow rate $Q$ may be increased, the cross-sectional area of the flow path $\Pi R^2$ may be decreased, or the length $L$ of the flow path may be increased.

For increasing an internal filtration rate and an internal backfiltration rate of a dialyzer, a dialyzer, the length of the flow path of which is increased by increasing total length (Japanese Patent Registration No. 2961481), and a dialyzer, the cross-sectional area of the blood flow path of which is decreased by decreasing the inner diameter of the hollow fiber membrane, (International Patent Application (PCT Pamphlet) WO 98/22161), have so far been known.

However, in the dialyzer with the total length increased, for obtaining effects of sufficient acceleration of internal filtration and internal backfiltration, the length of the flow path has to be increased to more than twice the length of the flow path in an ordinary dialyzer. Such a dialyzer is impractical. Further, in the dialyzer with the inner diameter of the hollow fiber membrane decreased, fluctuations occur in the inner diameter of the hollow fiber membrane during manufacture, which may increase blood remaining in lumens of the hollow fiber membranes after use of the dialyzer.

Further, there has been proposed, as a dialyzer in which a sectional area of a dialysate flow path is decreased by increasing a packing ratio of hollow fiber membranes, a dialyzer in which the hollow fiber bundle having more hollow fibers than ordinary hollow fiber bundles is shrunk with a net or the like and inserted in a case (Japanese Patent Application Laid-open No. Hei 08-168525 or International Patent Application (PCT Pamphlet) WO 98/22161). However, in the dialyzer with the hollow fiber bundle shrunk, the diameter of the hollow fiber bundle has to be decreased more than necessary in order to insert the hollow fiber bundle into a case. Therefore, the hollow fiber membranes might be ruptured and the packing ratio of the hollow fiber membranes inserted into the case is not high enough.

Moreover, as a dialyzer with a decreased cross-sectional area of a dialysate flow path, a dialyzer in which a substance having a property of being swelled with a dialysate is introduced in a dialysate flow path (International Patent Application (PCT Pamphlet) WO 98/22161 or Japanese Patent Application Laid-open No. Hei 08-192031 or Japanese Patent Application Laid-open No. Hei 11-009684), a dialyzer in which a bag-shaped member is introduced into a dialysate flow path and the bag-shaped member is swelled by introducing therein a physiological saline or the like at the time of using the dialyzer (International Patent Application (PCT Pamphlet) WO 98/22161 or Japanese Patent Application Laid-open No. Hei 11-000394 or Japanese Patent Application Laid-open No. Hei 11-319080), a dialyzer in which a hollow fiber bundle can be compressed together with a case with pressure applied from outside the case (Japanese Patent Application Laid-open No. Hei 11-319079) and the like have also been developed.

In a dialyzer in which a substance having a property of being swelled with a dialysate is introduced, the substance having the swelling property itself has a thickness so that an amount of the substance that can be introduced into the dialyzer is limited. When the amount of the substance having the swelling property is large, it is difficult to insert the hollow fiber bundle into the case of the dialyzer. On the other hand, when the amount of the substance having the swelling property is small, the cross-sectional area of the dialysate flow path is not sufficiently lowered. Further, in a dialyzer with the cylindrical substance having a swelling property introduced therein, it is difficult to insert the hollow fiber bundle into the lumen of the substance having the swelling property, because the substance has a far smaller inner diameter than the case, and the hollow fiber membranes might be ruptured. Further, in a dialyzer in which a bag-shaped member is swelled, or in a dialyzer in which a hollow fiber bundle is compressed together with a case, the structure is complicated and a force exerted in swelling the bag-shaped member or a force exerted by compression is also exerted on the case of the dialyzer. Thus, improvement in the case material is required so that the case has a satisfactory rigidity.

Moreover, a dialyzer with a cylindrical elastic tube has also been developed to contact hollow fibers with each other (French Patent Application No.2267138).

However, the elastic tube in this invention tightens a bundle of the hollow fibers and causes the hollow fibers to contact each other to prevent regular irrigation of dialysate. The cross-sectional area of the dialysate flow path cannot be decreased. Therefore the pressure loss along the dialysate flow path cannot be increased by the elastic tube in this invention.

Under these circumstances, an object of the present invention is to provide a dialyzer which can solve the foregoing problems associated with the conventional dialyzers. More specifically, an object of the present invention is to provide a dialyzer which is simple in structure without fear of rupturing hollow fiber membranes during fabrication and in which an internal filtration rate and an internal backfiltration rate are increased by decreasing the cross-sectional area of the dialysate flow path.

SUMMARY OF THE INVENTION

The inventors of the present invention have intensively conducted investigations and have consequently found that a dialyzer, which is provided with a cylindrical elastic tube inserted in a gap between an inner wall of a case of the dialyzer and a hollow fiber bundle, can solve the foregoing problems.

That is, according to the present invention, there is provided a dialyzer including a substantially cylindrical case, a hollow fiber bundle made of a plurality of hollow fiber membranes provided in the case, a blood flow path formed by lumens of the hollow fiber membranes, a dialysate flow path formed by gaps between the inner wall of the case and the hollow fiber membranes, and a cylindrical elastic tube inserted in a gap between the inner wall of the case and the hollow fiber bundle and gaps between the hollow fiber membranes.

The dialyzer of the present invention, which is provided with the elastic tube, has a decreased sectional area of the dialysate flow path and thereby increases the internal filtration rate and the internal backfiltration rate and performs filtration and replenishment of a greater volume of fluid. Such a structure gives the dialyzer a high dialysis efficiency. Moreover, in the method for manufacturing the dialyzer of the present invention, as the elastic tube is deformable, it is easy to first insert the hollow fiber bundle into the lumen of the elastic tube and then insert the hollow fiber bundle and the elastic tube into the case. Accordingly, the dialyzer can be manufactured without rupturing the hollow fiber membranes.

PREFERRED EMBODIMENTS OF THE INVENTION

The dialyzer of the present invention is described in detail below by referring to preferred embodiments shown in the appended drawings. However, the present invention is not limited to these embodiments.

Figure 1:
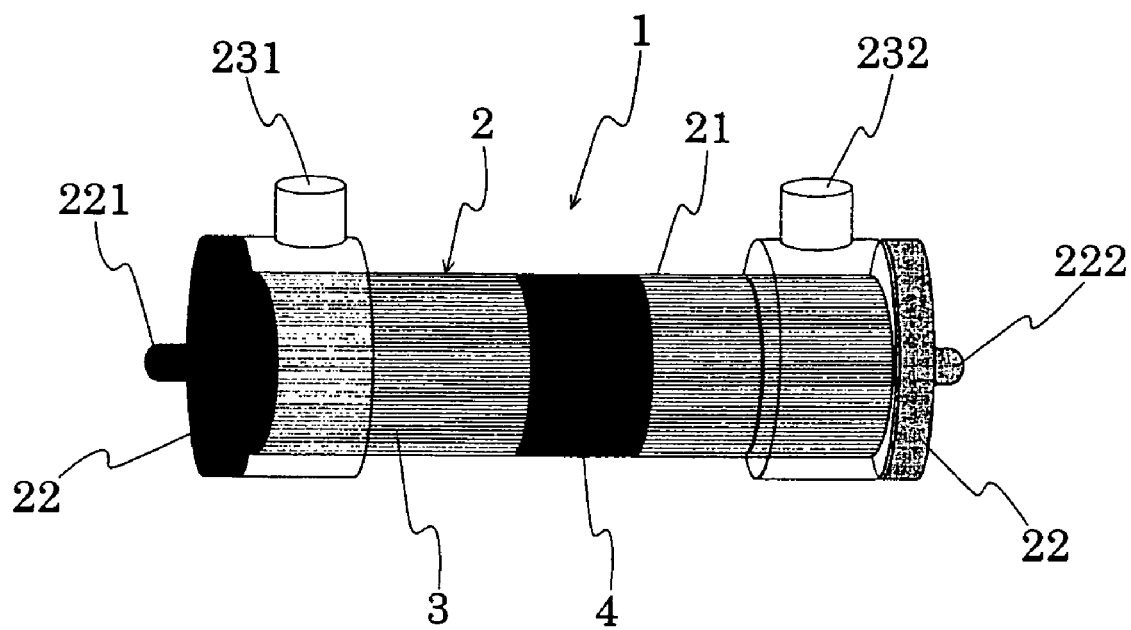
FIG. 1 is a perspective view showing a dialyzer according to an embodiment of the present invention.

As shown in FIG. 1, a dialyzer 1, which is an embodiment of the present invention, has a substantially cylindrical case 2 with both ends open into which both a hollow fiber bundle 3 made of a plurality of hollow fiber membranes 2 and an elastic tube 4 are inserted.

The case 2 in the dialyzer 1 of the present invention has a substantially cylindrical case body 21 with both ends open and a cap 22 mounted on each end of the case body 21. One of the caps 22 is provided with a blood inlet 221 and the other is provided with a blood outlet 222. The case body 21 is further provided with a dialysate outlet 231 and a dialysate inlet 232.

The case body 21 and the caps 22 are made of a hard resin such as, for example, polyethylene, polypropylene, and polycarbonate, acrylic resins such as polymethyl methacrylate, hard polyvinyl chloride, a styrene-butadiene copolymer, or polystyrene. For providing blood visibility inside the dialyzer 1, the material constituting the case body 21 and the caps 22 is preferably transparent or semitransparent. For discriminating between the blood inlet 221 and the blood outlet 222, the caps 22 may be formed of materials colored in different tints.

A hollow fiber bundle 3 made of a plurality of hollow fiber membranes is accommodated in the case 2. With respect to the hollow fiber membrane, polysulfone, polyethersulfone, polyacrylonitrile, polyamide, polyethylene, polypropylene, cellulose acetate, or regenerated cellulose is preferably used. It is desirable that an ultrafiltration rate (UFR) of the hollow fiber membrane is 20 mL/hr·m²·mmHg or more in order to surely remove unnecessary ingredients in blood.

The hollow fiber membranes are accommodated in the case 2 in a state of a hollow fiber bundle 3 obtained by bundling from 100 to 12,000 membranes. The effective membrane area of the hollow fiber membranes in the dialyzer is preferably from 0.1 to 3.0 m$^2$, and more preferably from 0.1 to 2.5 m$^2$. Further, the packing ratio of the hollow fiber membranes in the case 2 (the ratio of the total volume of the hollow fiber membranes to the inner volume of the cylindrical case) is preferably from 20 to 80%, and more preferably from 40 to 60%. The length and number of the hollow fiber membranes can be appropriately varied in order to acquire an effective cross sectional area of the membrane in the dialyzer. Also, the length of the case body can be varied according to the hollow fiber membranes.

The hollow fiber bundle 3 is fixed in the case 2 by injecting a potting agent in the gap between the inner wall of the case body 21 and the hollow fiber membranes on both ends of the hollow fiber bundle 3 and curing it, without clogging the lumens of the hollow fiber membranes. As the potting agent, polyurethane, silicone, epoxy resin or the like is preferably used. The potting agent closes a dialysate flow path, as described below, at both ends of the hollow fiber bundle 3 in order to prevent the dialysate passing through the dialysate flow path from flowing into the blood inlet 221 and the blood outlet 222 on the ends of the hollow fiber bundle 3.

In the dialyzer 1 of the present invention, the hollow fiber bundle 3 is accommodated in the case 2 to provide a dialysate flow path formed by the gap between the inner wall of the case 2 and the hollow fiber membranes and the gaps between the hollow fiber membranes and a blood flow path formed by the lumens of the hollow fiber membranes. One end of the dialysate flow path communicates with the dialysate outlet 231, and the other end communicates with the dialysate inlet 232. Further, one end of the blood flow path communicates with the blood inlet 221, and the other end communicates with the blood outlet 222. When the dialyzer is used, blood flows from the blood inlet 221 to the blood outlet 222 via the blood flow path. At this time, the dialysate flows from the dialysate inlet 232 located downstream of the blood flow path to the dialysate outlet 231 located upstream of the blood flow path via the dialysate flow path. Dialysis can be performed efficiently with the blood and the dialysate flowing in opposite directions through the hollow fiber membranes.

When a constricted portion is formed on the case body 21 of the dialyzer 1, the cross-sectional area of the dialysate flow path is decreased and a pressure loss along the dialysate is increased. As a result, internal filtration and internal backfiltration are accelerated. Therefore, the case body 21 in the dialyzer 1 of the present invention may have a constricted portion unless the insertion of the hollow fiber bundle 3 into the case 2 is hindered.

In addition, as described later, a concave portion for receiving and fixing the elastic tube 4 may be formed on the inner wall of the case body 21, so as to surely fix the elastic tube 4 in the case body 21.

In the dialyzer 1 of the present invention, the cylindrical elastic tube 4 is inserted in a gap between the inner wall of the case body 21 and the hollow fiber bundle 3. By providing the elastic tube 4, the sectional area of the dialysate flow path can be decreased to thereby cause a large pressure loss of the dialysate. Further, the hollow fiber membranes are fastened by the elastic tube 4 to thereby increase the packing ratio of the hollow fiber bundle 3 within the elastic tube 4. Therefore, it is possible to decrease the cross sectional area of the gaps between the hollow fiber membranes within the elastic tube 4 which form a flow path of the dialysate and further increase the pressure loss. Thereby, the internal filtration rate and the internal backfiltration rate are increased, giving the dialyzer high clearance and high dialysis efficiency.

The elastic tube 4 is formed of a material that makes the formed product deformable, such as, for example, silicone rubber, natural rubber, or synthetic rubber such as butadiene rubber. It is preferable that the elastic tube 4 formed of such materials is transparent or semitransparent.

The elastic tube 4 is inserted into the case body 21 with the hollow fiber bundle 3 inserted in the lumen of the elastic tube 4. An outer diameter of the elastic tube 4 is, though not particularly limited, preferably of such a size that the elastic tube 4 is easily inserted into the case body 21 with the hollow fiber bundle 3 inserted in the lumen of the elastic tube 4, and is water-tightly contacted with the inner wall of the case body 21 when the elastic tube 4 is inserted into the case body 21. Further, an inner diameter of the elastic tube 4 is of such a size that a packing ratio of the hollow fiber membranes is preferably from 50 to 85%, more preferably from 75 to 80%, when the elastic tube 4 is inserted into the case body 21. If the packing ratio of the hollow fiber membrane within the elastic tube 4 is less than 50%, a sufficient pressure loss of the dialysate cannot be obtained and sufficient internal filtration rate and an internal backfiltration rate cannot be obtained. If the packing ratio of the hollow fiber membrane is more than 80%, the hollow fiber membrane may collapse within the elastic tube 4.

Figure 2:
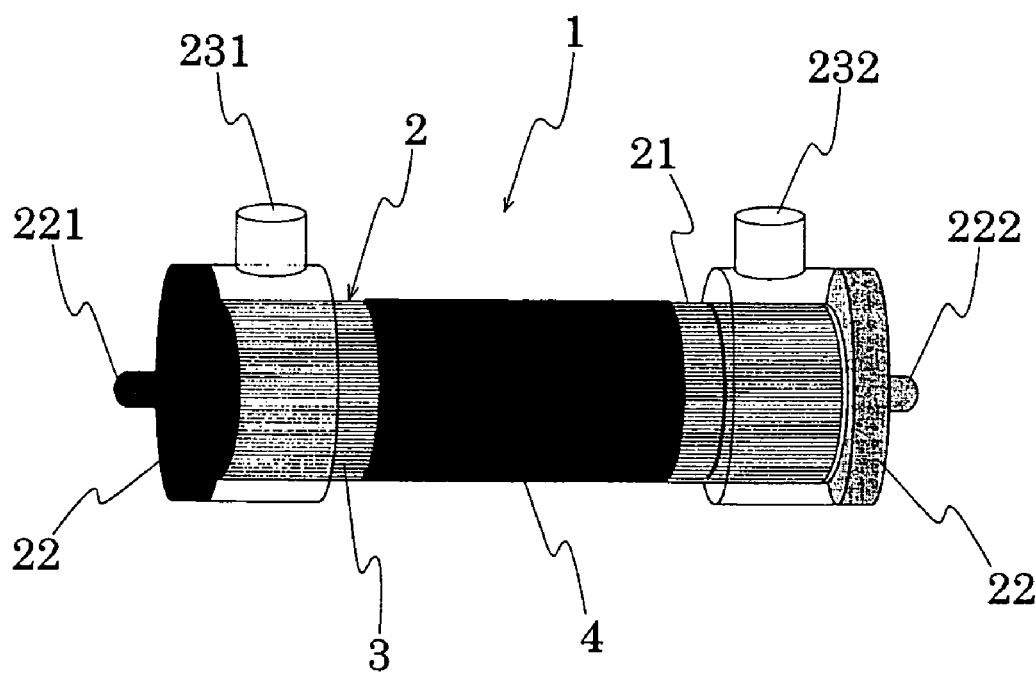
FIG. 2 is a perspective view showing a dialyzer according to another embodiment of the present invention.
Figure 3:
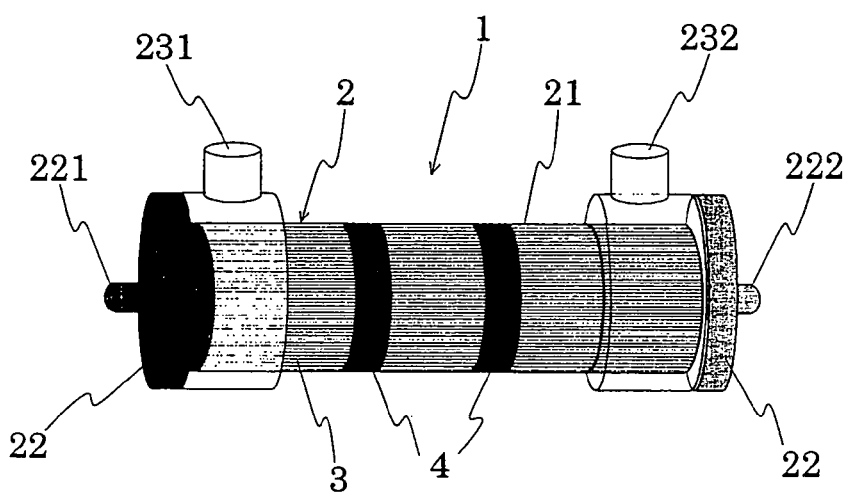
FIG. 3 is a perspective view showing the dialyzer according to still another embodiment of the present invention.
Figure 7:
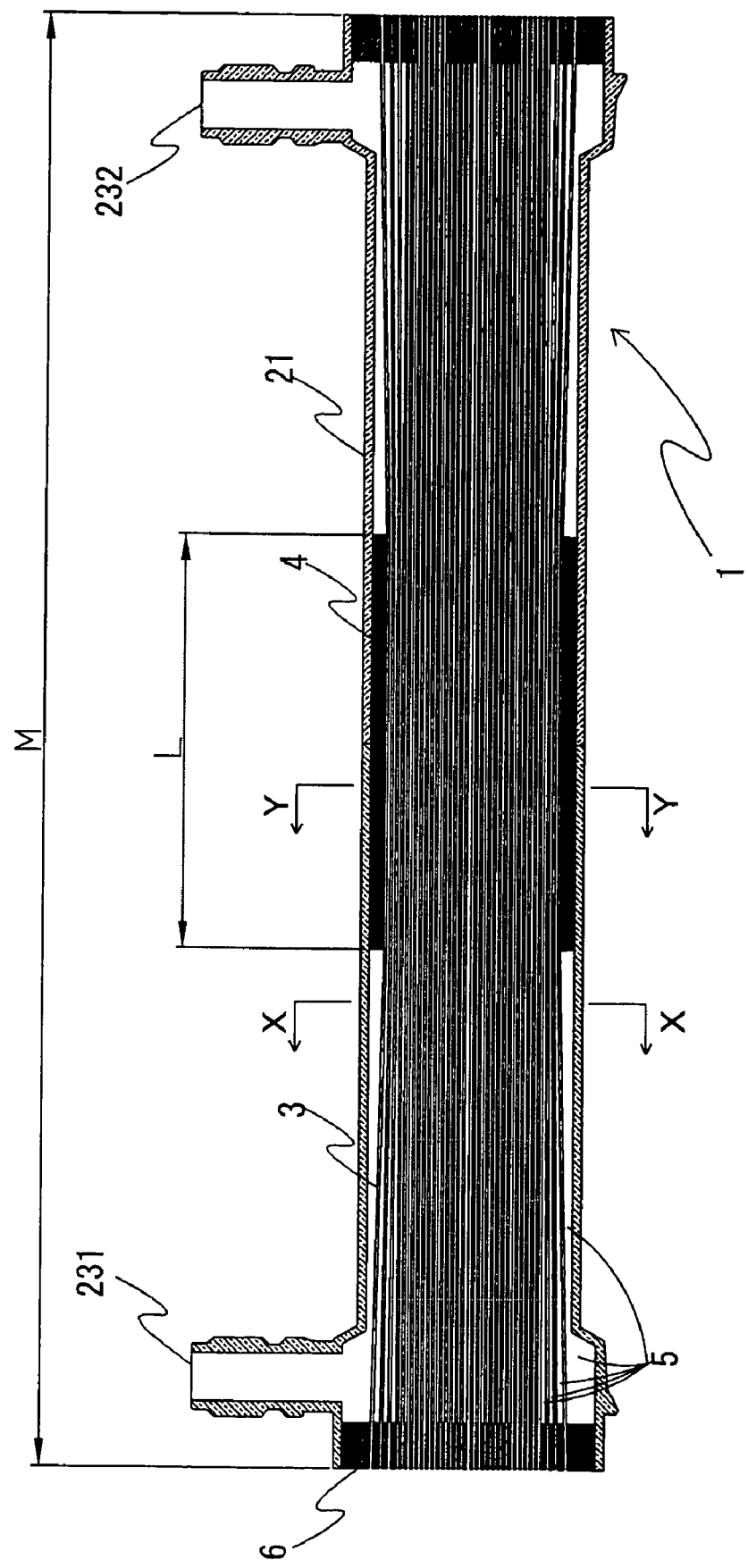
FIG. 7 is a cross sectional view of a dialyzer of Example 1 according to one embodiment of the present invention (caps 22 shown in FIG. 1 are not shown).
Figure 8:
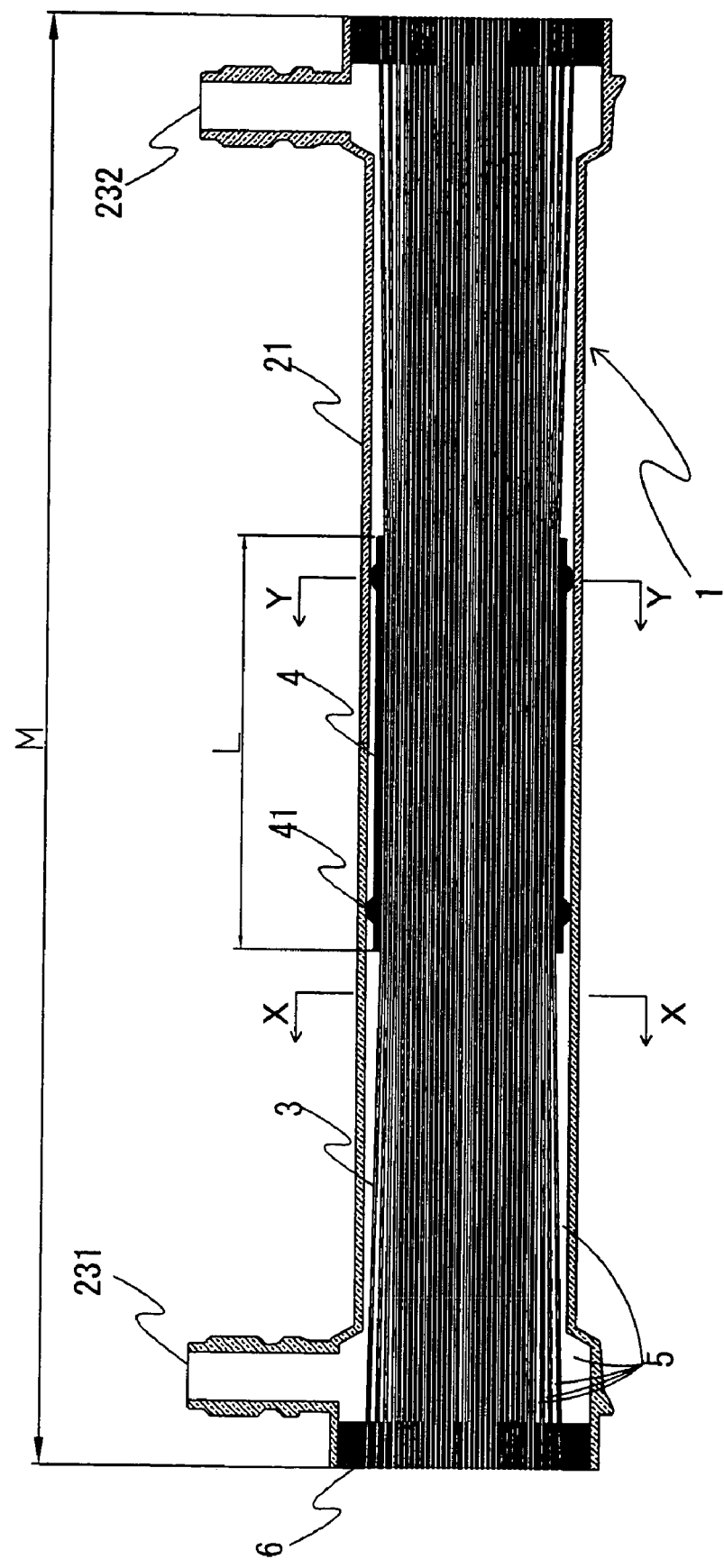
FIG. 8 is a cross sectional view of a dialyzer having the elastic tube shown in FIGS. 4A and 4B according to another embodiment of the present invention (caps 22 shown in FIG. 1 are not shown).
Figure 9:
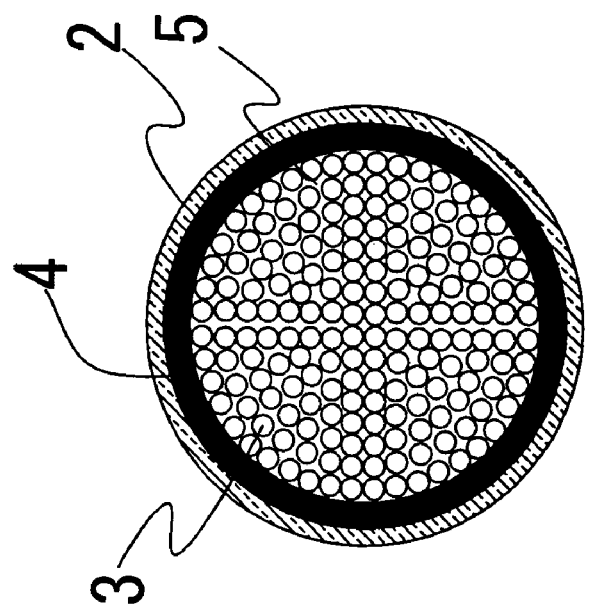
FIG. 9 is a cross sectional view of the dialyzer in each of FIG. 7 and FIG. 8 taken along X-X.
Figure 10:
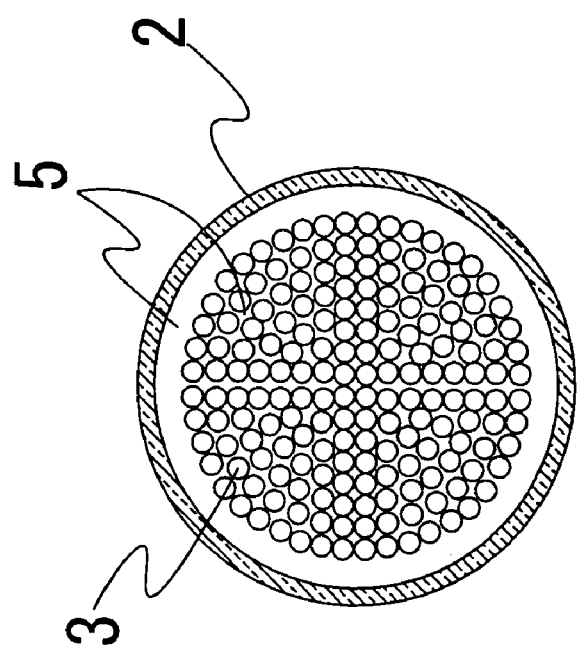
FIG. 10 is a cross sectional view of the dialyzer in each of FIG. 7 and FIG. 8 taken along Y-Y.

As shown in FIG. 2, the longer the elastic tube 4, the smaller the volume of the dialysate flow path becomes. The increase in the pressure loss of the dialysate increases the internal filtration rate and the internal backfiltration rate of the dialyzer 1, giving the dialyzer 1 a higher dialysis efficiency. The number of the elastic tubes 4 is not particularly limited; one elastic tube 4 that is long in the axial direction as shown in FIGS. 1 and 2 may be used, or two elastic tubes 4 that are short in the axial direction as shown in FIG. 3 may be used. The length L of the elastic tube 4 satisfies the following characteristics. As described above, the longer the elastic tube 4, the higher the dialysis efficiency of the dialyzer 1. Therefore, as shown in FIG. 7, the length L of the elastic tube 4 to the whole length M of the case body 21 in the dialyzer 1 is preferably 5% to 90%, more preferably, 10% to 80%, and, most preferably, 20% to 60%. Whole length M in the case body 21 in the dialyzer 1 is similar to the length of the hollow fiber bundle inserted therein. Because the tube has elasticity, it is easy to insert the elastic tube 4 containing the hollow fiber bundle into the case body 21. Therefore, the length L of the elastic tube 4 can be at most 90% of whole length M of the case body 21 in the dialyzer 1. Unless the tube has elasticity, such a long tube cannot be inserted into the case body 21 in the dialyzer 1. If the ratio of the length L of the elastic tube 4 to the whole length M of the dialyzer 1 is less than 5%, sufficient internal filtration rate and internal backfiltration rate cannot be obtained. If the ratio is more than 90%, it is undesirable that the dialysate cannot flow in and out of the gaps between the hollow fiber membranes within the hollow fiber bundle.

The dialysis efficiency of the dialyzer depends on the combination of the packing ratio of the hollow fiber membranes within the elastic tube 4 and the length L of the elastic tube 4. Several dialyzers having various acceptable lengths L of the elastic tube 4 and various acceptable packing ratios are prepared to select a suitable dialyzer having dialysis efficiency required in the dialysis therapy.

Subsequently, the inserted position of the elastic tube 4 is described herein. As shown in FIG. 7, a center of a lengthwise direction of the elastic tube 4 is preferably positioned at nearly the center of a lengthwise direction of the dialyzer 1. If the inserted position of the elastic tube 4 is at the extreme end of the dialyzer 1, the dialysate can flow in and out of the gaps between the hollow fiber membranes within the hollow fiber bundle with difficulty.

The elastic tube 4 is water-tightly contacted with the inner wall of the case body 21 by the elastic force of the tube, thereby surely fixing the elastic tube 4 in the case body 21. However, if water tightness between the elastic tube 4 and the inner wall of the case body 21 is high, which is effective in surely fixing the elastic tube 4 in the case body 21, it becomes more difficult to insert the elastic tube 4 into the case body 21.

Figure 4A:
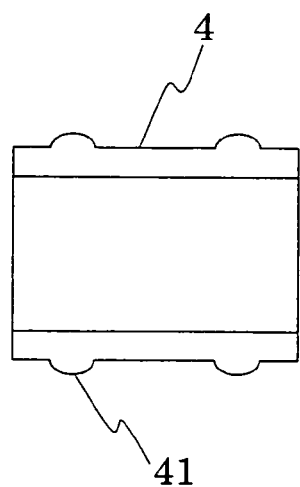
FIGS. 4A and 4B are, respectively, cross sectional views showing an elastic tube 4 of a dialyzer according to an embodiment of the present invention and showing a case body 21 provided on the inner surface with a concave portion adapted with a rib on the elastic tube.
Figure 4B:
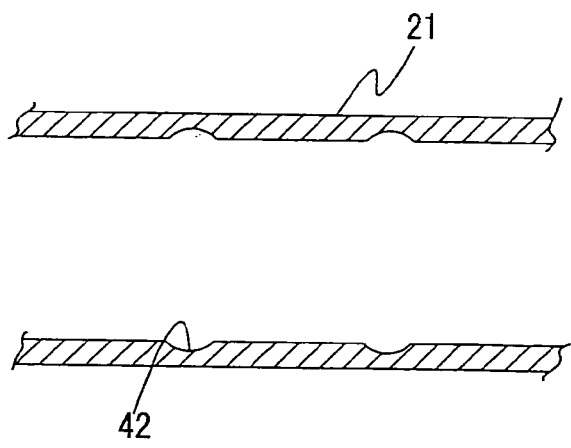

Accordingly, a ring rib 41 may be formed on an outer surface of the elastic tube 4 as shown in FIG. 4A, so that the elastic tube 4 is easily inserted into, and surely fixed in, the case body 21. The number of the ring ribs 41 is not particularly limited; for example, two ring ribs 41 may be respectively formed on both ends of the elastic tube 4 as shown in FIG. 4A.

Further, to insert the elastic tube 4 into the case body 21 more easily, a lubricant such as a glycerin may be applied to the outer surface of the elastic tube 4 or the inner wall of the case body 21. If such a lubricant is applied to the inner surface of the elastic tube 4 as well, the hollow fiber bundle 3 may also be inserted more easily into the lumen of the elastic tube 4.

In addition, as described earlier, a concave portion 42 for receiving and fixing the elastic tube 4 may be formed on the inner wall of the case body 21 so as to surely fix the elastic tube 4 in the case body 21.

Next, referring to FIG. 5, a method for manufacturing the dialyzer 1 shown in FIG. 1 according to the present invention will be described.

First, the hollow fiber bundle 3 made of the plurality of hollow fiber membranes is inserted into the lumen of the cylindrical elastic tube 4. More specifically, the elastic tube 4 shown in FIG. 5(1) is deformed to have an enlarged diameter as shown in FIG. 5(2). There are a variety of methods for deforming the elastic tube: a method in which the outer surface of the elastic tube 4 is pulled outward by vacuum suction, a method in which a taper jig etc. is inserted into the lumen of the elastic tube 4 to enlarge the lumen, or the like. Next, as shown in FIG. 5(3), the hollow fiber bundle 3 is inserted into the elastic tube 4 whose lumen has been enlarged. Then, the elastic tube 4 is restored to its original state as shown in FIG. 5(4). Next, as shown in FIG. 5(5), the elastic tube 4 and the hollow fiber bundle 3 inserted therein are inserted into the case body 21.

The foregoing processes are the most characteristic processes in the method for producing the dialyzer 1 according to the present invention which is characterized by having the elastic tube 4. The case body 21 with the elastic tube 4 and the hollow fiber bundle 3 inserted therein, which is obtained through the foregoing processes, will thereafter undergo the same manufacturing processes as the conventional dialyzers. That is, a potting agent is injected into both ends of the case body 21 to fix the hollow fiber bundle 3 in the case body 21, followed by mounting of the caps 22 on the ends of the case body 21 and so on, to thereby manufacture a dialyzer.

Figure 5:
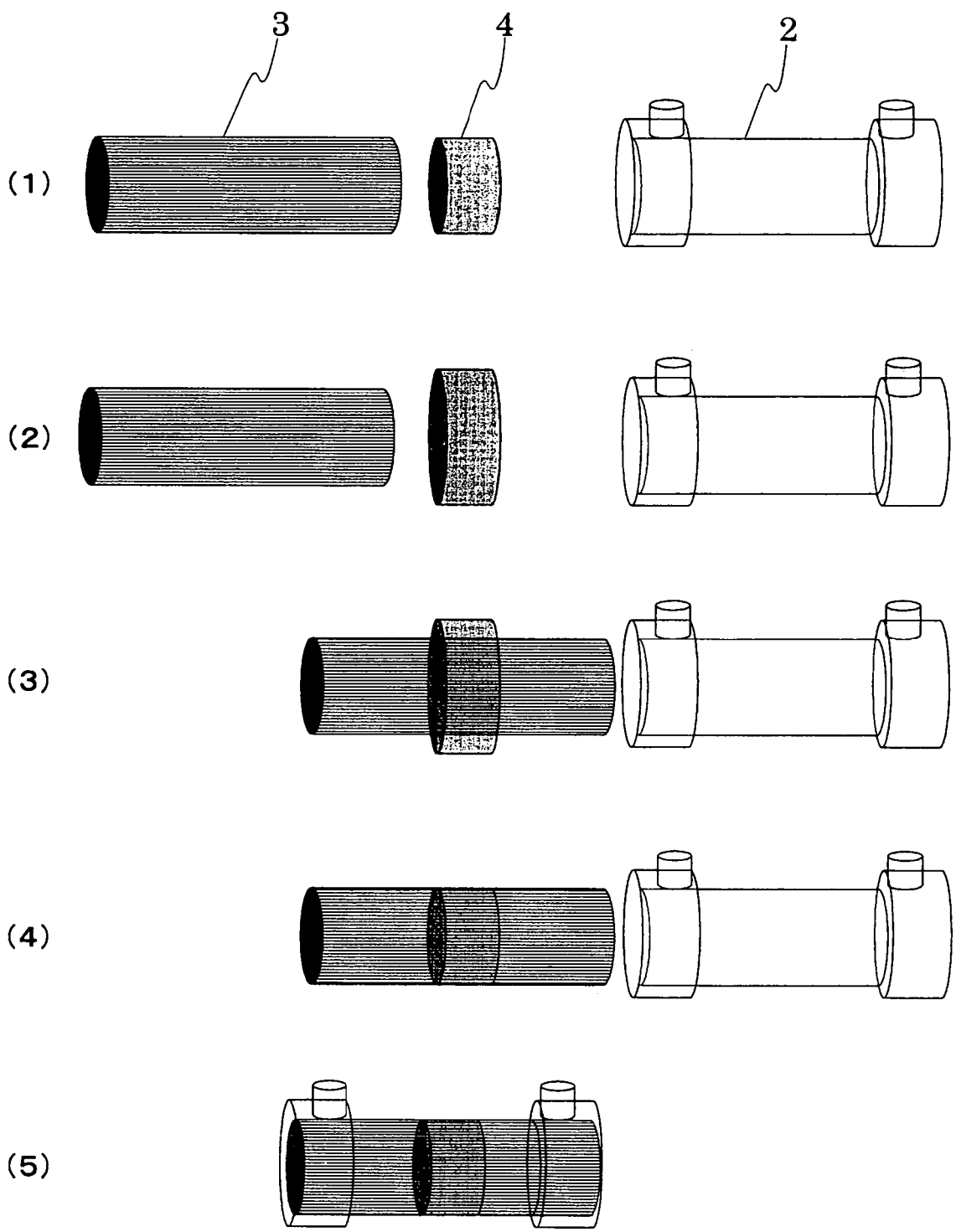
FIG. 5 is a diagram for explaining a method for manufacturing a dialyzer according to the present invention.

The process of enlarging the lumen of the elastic tube 4 as shown in FIG. 5 can be omitted in the case where it is not difficult to insert the hollow fiber bundle 3 into the lumen of the elastic tube 4, that is, in the case where a lubricant is applied to the inner surface of the elastic tube 4, for example.

Further, a known tool for insertion may be used if required in the process of inserting the hollow fiber bundle 3 into the elastic tube 4 and the process of inserting the elastic tube 4 and the hollow fiber bundle 3 inserted therein into the case body 21.

Figure 6:
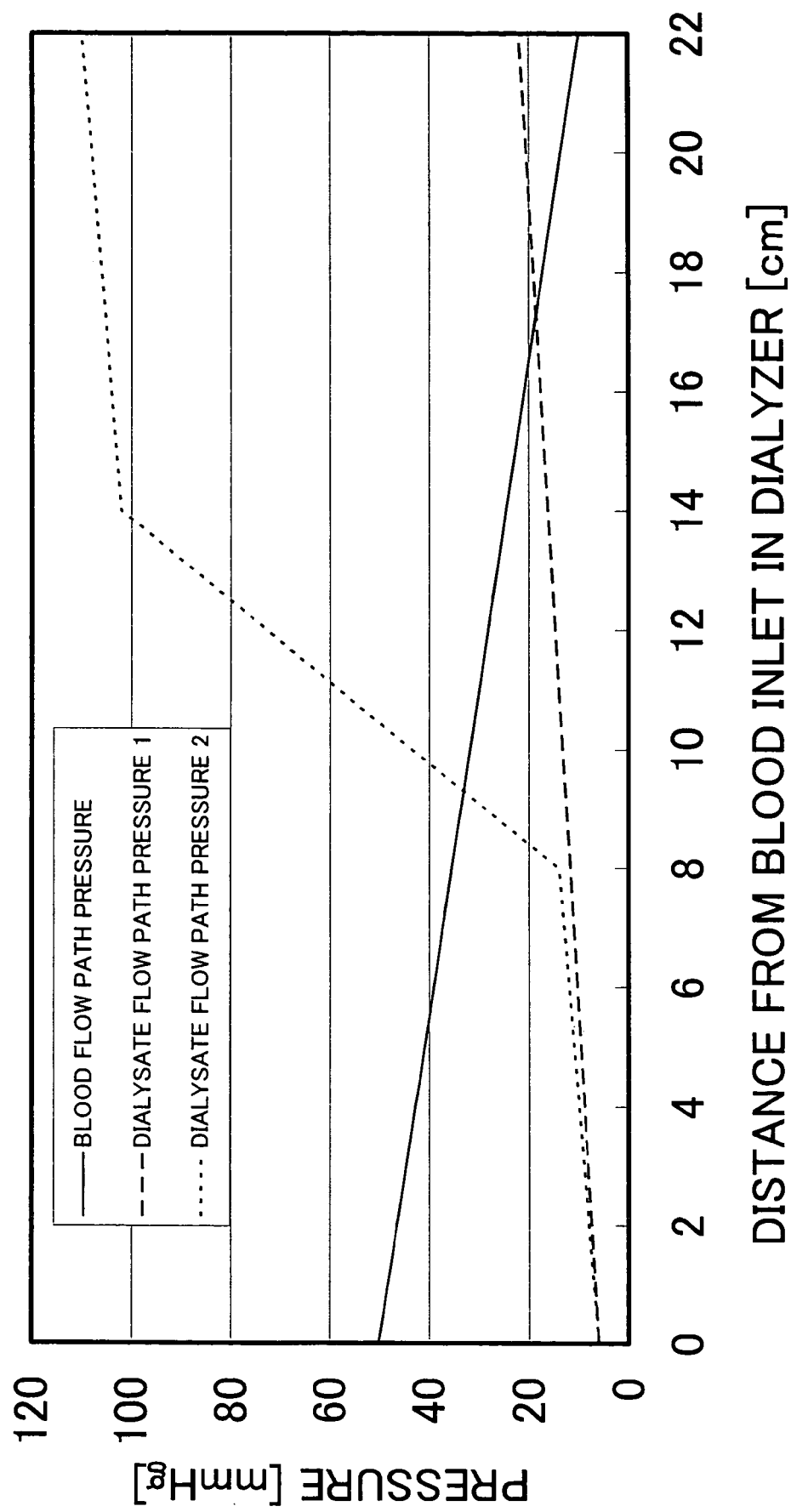
FIG. 6 is a graph showing pressure distribution of a fluid in a blood flow path and a dialysate flow path in a dialyzer according to the present invention.

FIG. 6 is a graph showing pressure distribution of a fluid in the blood flow path and the dialysate flow path in the dialyzer when the blood and the dialysate flow in the dialyzer of the present invention.

The internal filtration and the internal backfiltration of the dialyzer occur by a difference between the blood flow path pressure and the dialysate flow path pressure (transmembrane pressure difference TMP). As shown by a line indicating the blood flow path pressure and a line indicating the dialysate flow path pressure 1 in the graph, the internal filtration occurs in the vicinity of the blood outlet (left side in the graph) because the blood flow path pressure is higher than the dialysate flow path pressure of the dialysate flow path. The internal backfiltration occurs in the vicinity of the blood outlet (right side in the graph) because the blood flow path pressure is lower than the dialysate flow path pressure. As the TMP becomes greater, the internal filtration and the internal backfiltration of a larger amount of fluid occur. The difference between the internal backfiltration rate and the internal filtration rate (internal backfiltration rate minus internal filtration rate) corresponds to a dewatering rate. The dewatering rate is controlled for each patient undergoing dialysis by a dewatering rate controller incorporated in a general equipment for dialysis.

In the dialyzer 1 of the present invention, the elastic tube 4 is used for increasing the TMP. The use of the elastic tube 4 decreases the cross-sectional area of the dialysate flow path. As a result of the decrease in the cross-sectional area of the dialysate flow path, the dialysate flow path pressure is abruptly increased at the portion in which the elastic tube 4 is inserted as shown by a line indicating the dialysate flow path pressure 2 in the graph. As a result, the TMP is increased to allow the internal filtration and the internal backfiltration of a large amount of fluid.

EXAMPLES

Examples that specifically illustrate the present invention are described below.

Example 1

A jig with a vacuum suction function was used to enlarge a lumen of an elastic tube with a rib made of silicone rubber. The elastic tube has an inner diameter of 28.5 mm, an outer diameter of 36 mm, a length of 20 mm (L/M=about 7.35%), and an outer diameter of 37.5 mm at the portion where the rib was formed. A hollow fiber bundle obtained by bundling approximately 9,000 hollow fiber membranes each made of polyethersulfone and having an inner diameter of 200 μm and an outer diameter of 260 μm was inserted into the lumen of the tube. Then, the elastic tube was restored to its original state. Subsequently, the elastic tube with the hollow fiber bundle inserted therein was inserted into a central portion of a case body of a dialyzer made of polycarbonate and having a total length of 272 mm and an inner diameter of 36.5 mm. In Example 1, a glycerin serving as a lubricant was applied in advance to an inner wall of the case body and an outer surface of the elastic tube. Then, a potting agent was injected into both ends of the case body to fix the hollow fiber bundle in the case body. An effective membrane area of the hollow fiber bundle was 1.5 $m^2$, and a packing ratio of the hollow fiber bundle was 45%. Caps were then mounted on both ends of the case body to manufacture a dialyzer. In the dialyzer, the packing ratio of the hollow fiber membranes in the lumen of the elastic tube was 79%.

Example 2

A dialyzer was manufactured in the same manner as in Example 1, the only difference being the use of an elastic tube with a rib made of silicone rubber having an inner diameter of 28.5 mm, an outer diameter of 36 mm, a length of 40 mm (L/M=about 14.71%), and an outer diameter of 37.5 mm at the portion where the rib was formed. In the dialyzer, the packing ratio of the hollow fiber membranes in the lumen of the elastic tube was 79%.

Example 3

A dialyzer was manufactured in the same manner as in Example 1, the only difference being the use of an elastic tube with a rib made of silicone rubber having an inner diameter of 28.5 mm, an outer diameter of 36 mm, a length of 60 mm (L/M=about 22.06%), and an outer diameter of 37.5 mm at the portion where the rib was formed. In the dialyzer, the packing ratio of the hollow fiber membranes in the lumen of the elastic tube was 79%.

Example 4

A dialyzer was manufactured in the same manner as in Example 1, the only difference being the use of an elastic tube having an inner diameter and an outer diameter such that the packing ratio of the hollow fiber membrane within the elastic tube was 65% and having a length of 60 mm (L/M=about 22.06%).

Example 5

A dialyzer was manufactured in the same manner as in Example 1, the only difference being the use of an elastic tube having an inner diameter and an outer diameter such that the packing ratio of the hollow fiber membrane within the elastic tube was 65% and having a length of 120 mm (L/M=about 44.12%).

Comparative Example 1

A hollow fiber bundle obtained by bundling approximately 9,000 hollow fiber membranes each made of polyethersulfone and having an inner diameter of 200 μm and an outer diameter of 260 μm was inserted into a lumen of a case body of a dialyzer made of polycarbonate and having a total length of 272 mm and an inner diameter of 36.5 mm. A potting agent was injected into both ends of the case body to fix the hollow fiber bundle in the case body. An effective membrane area of the hollow fiber bundle was 1.5 m², and a packing ratio of the hollow fiber bundle was 45%. Caps were then mounted on each of the ends of the case body to manufacture a dialyzer.

A dialysate was passed through the dialysate flow path of the dialyzer obtained in each of Examples 1 to 5 and Comparative Example 1 at a flow rate of 500 mL/min, and a pressure loss of the dialysate was measured by measuring pressures of the dialysate at the dialysate inlet and the dialysate outlet. The results are shown in Table 1.

Further, clearance of $\beta_2$ microglobulin (molecular weight of 11,800) was measured using the dialyzer obtained in each of Examples 1 to 5 and Comparative Example 1, based on performance evaluations and function classification of devices for blood purification established by Japanese Society for Dialysis Therapy (Journal of the Japanese Society for Dialysis Therapy, Vol.29 No.8, 1231-1245, 1996). The measurement was conducted after a dialysis of bovine blood for 60 minutes. Bovine blood (Ht=30%, total protein concentration 6.5 g/dL, $\beta_2$ microglobulin concentration 1 mg/L, 37° C.) was used for the measurement. The measurement conditions were as follows: blood flow rate 200 mL/min, dialysate flow rate 500 mL/min, and dewatering rate 15 mL/min. The measurement results are shown in Table 1.

TABLE 1

| Ex. | Packing ratio of hollow fiber within elastic tube (%) | Length of elastic tube [mm] | Pressure loss [mmHg] | Clearance [mL/min] |
|---|---|---|---|---|
| 1 | 79 | 20 | 29 | 69 |
| 2 | 79 | 40 | 52 | 87 |
| 3 | 79 | 60 | 77 | 110 |
| 4 | 65 | 60 | 20 | 73 |
| 5 | 65 | 120 | 43 | 84 |
| Com. Ex. 1 | — | — | 10 | 58 |

As shown in Table 1, it is found that the pressure loss of the dialysate in the dialyzer of the present invention in Examples 1 to 5 is significantly increased in comparison to the pressure loss of the dialysate in the conventional dialyzer in Comparative Example 1. It is further found that the clearance of $\beta_2$ microglobulin in the dialyzer of the present invention in Examples 1 to 5 is increased in comparison to the clearance in the conventional dialyzer in Comparative Example 1.

Therefore, it is obvious that the dialyzer having high dialysis efficiency can be obtained. From the result in Example 4 in which the length of the elastic tube is same as that in Example 3 but the packing ratio of the hollow fiber membrane within the elastic tube is decreased more than that in Example 3, it is also obvious that the clearance is increased as the packing ratio of the hollow fiber membrane is higher. Further, the clearance is increased according to the length of the elastic tubes in the dialyzers which have the same packing ratio of the hollow fiber membrane within the elastic tube (See, Example 1 to 3, and Example 4 and 5). Therefore, even if the packing ratio of the hollow fiber membrane within the elastic tube is decreased in order to protect the hollow fiber membrane, a dialyzer having high dialysis efficiency can be obtained by increasing the length of the elastic tube.

The results reveal that the dialyzer of the present invention, which is provided with the elastic tube is, in comparison to the conventional dialyzer (Comparative Example 1) not having the elastic tube, decreased in the cross-sectional area of the dialysate flow path and thereby increases the internal filtration rate and the internal backfiltration rate. The clearance is increased.

INDUSTRIAL APPLICABILITY

The dialyzer of the present invention can increase the flow rate of internal filtration and the flow rate of internal backfiltration by providing an elastic tube. Further, since the cross-sectional area of the dialysate flow path is sufficiently decreased by the elastic tube, the flow rate of internal filtration and the flow rate of internal backfiltration can easily be increased. Moreover, as the dialyzer of the present invention uses an elastic tube that is deformable, the lumen of the elastic tube is easily enlarged and the dialyzer can easily be manufactured without fear of rupturing the hollow fiber membranes.

What is claimed is:

1. A dialyzer comprising a substantially cylindrical case having a length M, a hollow fiber bundle made of a plurality of hollow fiber membranes provided in the case, a gap formed between an inner wall of the case and the hollow fiber bundle, a blood flow path formed by lumens of the hollow fiber membranes, a blood inlet to and a blood outlet from the blood flow path, a dialysate flow path formed by the gap between the inner wall of the case and the hollow fiber membranes and gaps between the hollow fiber membranes, a dialysate inlet to and a dialysate outlet from the dialysate flow path, and a cylindrical elastic tube having a length L inserted in the gap between the inner wall of the case and the hollow fiber bundle and substantially contacting the inner wall of the case,
    wherein L is 5% to 90% of M;
    a lubricant is provided between an outer surface of the elastic tube and the inner wall of the case;
    a rib is formed on an outer circumferential surface of the elastic tube;
    a concave portion for receiving the rib and fixing the elastic tube is formed on an inner wall of the case;
    the rib is fitted into the concave portion so that the elastic tube is securely fixed in the case; and
    the elastic tube is water-tightly contacted with the inner wall of the case by the elastic force of the tube, thereby securely fixing the elastic tube in the case.

2. A dialyzer according to claim 1, wherein the cylindrical elastic tube comprises a plurality of elastic tubes.

3. A dialyzer according to claim 1, wherein L is 10% to 80% of M.

4. A dialyzer according to claim 1, wherein L is 20% to 60% of M.

5. A dialyzer according to claim 2, wherein L is 10% to 80% of M.

6. A dialyzer according to claim 2, wherein L is 20% to 60% of M.

* * * * *